(12) United States Patent
Tajima

(10) Patent No.: US 10,676,707 B2
(45) Date of Patent: Jun. 9, 2020

(54) CULTURE SYSTEM AND CULTURE METHOD

(71) Applicant: Universal Bio Research Co., Ltd., Matsudo-shi, Chiba (JP)

(72) Inventor: Hideji Tajima, Matsudo (JP)

(73) Assignee: Universal Bio Research Co., Ltd., Matsudo-shi, Chiba (JP)

( * ) Notice: Subject to any disclaimer, the term of this patent is extended or adjusted under 35 U.S.C. 154(b) by 144 days.

(21) Appl. No.: 14/916,764

(22) PCT Filed: Sep. 2, 2014

(86) PCT No.: PCT/JP2014/072975
§ 371 (c)(1),
(2) Date: Mar. 4, 2016

(87) PCT Pub. No.: WO2015/037468
PCT Pub. Date: Mar. 19, 2015

(65) Prior Publication Data
US 2016/0201023 A1    Jul. 14, 2016

(30) Foreign Application Priority Data

Sep. 12, 2013   (JP) ................................ 2013-189715

(51) Int. Cl.
*C12M 1/00*        (2006.01)
*C12M 3/00*        (2006.01)
(Continued)

(52) U.S. Cl.
CPC ............ *C12M 47/02* (2013.01); *C12M 21/08* (2013.01); *C12M 23/00* (2013.01); *C12M 23/28* (2013.01);
(Continued)

(58) Field of Classification Search
CPC ...................................................... C12M 47/02
(Continued)

(56) References Cited

U.S. PATENT DOCUMENTS 5,250,432 A * 10/1993 Takashiki ............... C12M 47/02
                                                            435/383
5,536,475 A *  7/1996 Moubayed ............. A61K 35/16
                                                            209/217
(Continued)

FOREIGN PATENT DOCUMENTS

EP          0753573 A2    1/1997
EP          2639294 A1    9/2013
(Continued)

OTHER PUBLICATIONS

Dobson et al., "Principles and Design of a Novel Magnetic Force Mechanical Conditioning Bioreactor for Tissue Engineering, Stem Cell Conditioning, and Dynamic In Vitro Screening," Sep. 2006, IEEE Transactions on Nanobioscience, vol. 5 No. 3 (Year: 2006).*

(Continued)

*Primary Examiner* — Kevin Joyner
*Assistant Examiner* — Holly Kipouros
(74) *Attorney, Agent, or Firm* — Troutman Sanders LLP

(57) ABSTRACT

A culture system comprises: a preparatory culture vessel and a main culture vessel that accommodate cells and a solution; a main stage that holds the preparatory culture vessel and the main culture vessel; a connecting tube that connects the culture vessels; a valve that opens and closes the connecting tube; and a rotating mechanism that rotates the main stage and imparts a height difference between the culture vessels to transfer the cells and solution by dropping between the culture vessels.

22 Claims, 2 Drawing Sheets

(51) Int. Cl.
*C12M 1/36* (2006.01)
*C12M 1/42* (2006.01)
*C12N 5/071* (2010.01)

(52) U.S. Cl.
CPC ............ *C12M 23/34* (2013.01); *C12M 29/00* (2013.01); *C12M 35/06* (2013.01); *C12M 41/48* (2013.01); *C12N 5/0602* (2013.01)

(58) Field of Classification Search
USPC ...................................................... 435/286.5
See application file for complete search history.

(56) References Cited

U.S. PATENT DOCUMENTS

| | | | |
|---|---|---|---|
| 6,312,950 | B1 | 11/2001 | Ohmura et al. |
| 2003/0054335 | A1 | 3/2003 | Taya et al. |
| 2005/0239196 | A1 | 10/2005 | Yanai et al. |
| 2008/0057573 | A1* | 3/2008 | Hutchins ................. G01N 1/36 435/307.1 |
| 2009/0137026 | A1* | 5/2009 | Kobayashi ............. C12M 23/12 435/286.4 |
| 2009/0203082 | A1 | 8/2009 | Schlaubitz et al. |
| 2013/0190212 | A1* | 7/2013 | Handique ......... B01L 3/502715 506/37 |
| 2014/0377739 | A1* | 12/2014 | Welch .................... C12M 47/02 435/3 |

FOREIGN PATENT DOCUMENTS

| | | |
|---|---|---|
| JP | 64-1843333333 A | 1/1989 |
| JP | S64005486 A | 1/1989 |
| JP | 3-7575 A | 1/1991 |
| JP | 2000083649 A | 3/2000 |
| JP | 2001275659 A | 10/2001 |
| JP | 2004-097045 A | 4/2004 |
| JP | 2004097046 A | 4/2004 |
| JP | 2005095165 A | 4/2005 |
| JP | 2005198626 A | 7/2005 |
| JP | 2006006219 A | 1/2006 |
| JP | 2008079554 A | 4/2008 |
| JP | 2008534935 A | 8/2008 |
| JP | 2009159890 A | 7/2009 |
| WO | 02/051985 A2 | 7/2002 |
| WO | 2009/088023 A1 | 7/2009 |

OTHER PUBLICATIONS

Extended European Search Report dated Mar. 10, 2017 issued in corresponding European Patent Application No. 14843505.0.
International Search Report and PCT Written Opinion issued in corresponding PCT International Application No. PCT/JP2014/072975.

* cited by examiner

CULTURE SYSTEM AND CULTURE METHOD

CROSS-REFERENCE TO RELATED APPLICATIONS

This application is a US National Stage of International Application No. PCT/JP2014/072975, filed Sep. 2, 2014, which claims the benefit of Japanese Patent Application No. 2013-189715, filed Sep. 12, 2013, the entire contents of each of which applications are hereby incorporated by reference.

TECHNICAL FIELD

The present invention relates to a culture system and a culture method that perform cell culture using dropping of a solution.

BACKGROUND ART

Adherent cells such as somatic cells adhere to the bottom surface of a culture vessel and form a foothold before repeating cell division and cell elongation to increase the number thereof. In this regard, if the increase in the cell number keeps going on, the cells start to scramble for adhesion area on the bottom surface of the vessel since the cells remain adhered to the bottom surface of the culture vessel. Therefore, if the increase in the cell number continues, there will be no space between the cells and eventually the cells will be multi-layered, due to which the cells will suffocate without sufficient nutrients (confluent condition) and result in dead cells.

Accordingly, when adherent cells are cultured in a culture vessel, culture needs to be performed while detaching the cells from the culture vessel and transferring them to other vessel at a given cell number (given density) before reaching the confluent condition so as to keep sufficient nutrients to go throughout the adherent cells (subculture).

In order to detach the cells from the culture vessel and transfer them into other vessel, there is a need to use an enzyme solution such as trypsin to degrade the cell adhesion protein to allow the cells to float or use a scraper to physically detach the cells from the culture vessel. In the field of cell culture, it is well known that these methods are unfavorable treatments since they will place stress on the cells. For example, trypsin is known to be toxic to cells and it is known that a trypsin treatment will change the property of the cells and result dead cells. Therefore, it is desirable to minimize such treatments as much as possible that will place stress on cells.

In addition, the operation of detaching adherent cells from a culture vessel and transferring them into other vessel is manually conducted in a clean bench. Manual operations are constantly at a risk of contamination.

SUMMARY OF THE INVENTION

Furthermore, in a case of a large volume culture solution (several hundreds ml), there is a need of performing efficient cell culture in an automatic manner without manually transferring the solution.

Accordingly, in order to subculture adherent cells, the adherent cells need to be moved to another position so as to provide the cells with new environment where they can absorb nutrients, for example, by transferring them into other vessel or the like by manual operation that is associated with a risk of contamination and that places stress on the adherent cells. Thus, automation has been difficult.

An objective of the present invention is to provide a culture system and method which are capable of automating cell culture by dispersing cells such as adherent cells in a solution and controlling the transfer of the cell-dispersed solution.

In order to solve the above-described problem, the present inventor has gone through keen study, as a result of which succeeded in automatically performing seeding through collection of the cells with less stress on the cells in a sterile state, in the a case of culturing adherent cells, by using an adherent cell mass or by attaching adherent cells onto magnetic particles or a carrier that adsorbs to the particles to allow the cells to disperse in a solution and transferring the solution into the culture vessel or transferring the solution from the culture vessel to outside by height-difference transfer, thereby accomplishing the present invention.

Thus, the present invention is as follows.

(1) A culture system including a plurality of housing vessels for accommodating cells and a solution; conduits for connecting the plurality of housing vessels; an opening-closing mechanism for opening and closing the conduits; and a height-difference imparting mechanism for imparting a height difference between the plurality of housing vessels in order to allow dropping of the cells and the solution between the plurality of housing vessels.

(2) The culture system according to (1), comprising a first holding section for holding the plurality of housing vessels. (3) The culture system according to (1), wherein the height-difference imparting mechanism imparts a height difference to at least one of the plurality of housing vessels by moving the first holding section. (4) The culture system according to any one of (1) to (3), wherein the plurality of housing vessels comprise one or a plurality of culture vessels. (5) The culture system according to any one of (1) to (4), wherein at least one of the plurality of housing vessels is connected to at least one cylinder or bellows vessel. (6) The culture system according to any one of (1) to (5), wherein the height-difference imparting mechanism imparts a height difference between the housing vessel and the cylinder or the bellows vessel so as to transfer the cells and the solution between the housing vessel and the cylinder or the bellows vessel by dropping.

(7) The culture system according to (6), wherein the cylinder or the bellows vessel is a waste fluid vessel, and the conduit connecting between the waste fluid vessel and the housing vessel is provided with a cell capturing unit. (8) The culture system according to (7), wherein the cylinder or the bellows vessel is a feed fluid vessel, which is connected to the cell capturing unit. (9) The culture system according to (8), comprising a switching mechanism for switching between the connection between the cell capturing unit and the waste fluid vessel and the connection between the cell capturing unit and the feed fluid vessel. (10) The culture system according to any one of (5) to (9), comprising a stretching mechanism for stretching the cylinder or the bellows vessel.

(11) The culture system according to any one of (5) to (10), comprising a first holding section for holding at least one of the housing vessels and a second holding section for holding the cylinder or the bellows vessel. (12) The culture system according to (11), wherein the first holding section and the second holding section are detachable. (13) The culture system according to any one of (1) to (12), wherein the housing vessels are provided with a temperature regulating unit. (14) The culture system according to any one of (1) to (13), wherein the housing vessels are provided with a carbon dioxide supply section. (15) The culture system according to any one of (1) to (14), wherein the housing vessels are provided with a ventilation section. (16) The culture system according to any one of (1) to (15), wherein the housing vessels are disposable.

(17) The culture system according to any one of (5) to (12), wherein the bellows vessel is disposable. (18) The culture system according to any one of (1) to (17), comprising a swing mechanism for swinging the housing vessels.

(19) The culture system according to any one of (1) to (18), comprising magnetic particles that are attached to the cells in the solution, a magnet provided outside the culture vessel and a magnetic force regulating unit for regulating the magnetic force of the magnet, wherein the magnetic force regulating unit regulates the magnetic force of the magnet to shake or vibrate the magnetic particles and the cells in the culture vessel. (20) The culture system according to any one of (1) to (19), comprising a controller for controlling the opening-closing mechanism and the height-difference imparting mechanism, wherein the controller controls the opening-closing mechanism and the height-difference imparting mechanism according to a predetermined procedure to perform cell culture and transfer the solution in an automatic manner.

(21) A method for performing cell culture by using the culture system according to any one of (1) to (20). (22) The method according to (21), comprising the steps of: culturing at a position where the height difference between the plurality of housing vessels is made smaller by the height-difference imparting mechanism; transferring the cells and the solution at a dropping position where the height difference between the plurality of housing vessels is made larger by the height-difference imparting mechanism; and treating the solution using at least one cylinder or bellows vessel connected to at least one of the plurality of housing vessels. (23) The method according to (22), wherein the step of treating the solution is a step of discarding the solution or a step of supplying the solution.

According to the present invention, cell culture can be performed while automatically controlling the position of the cells such that the cells can absorb nutrients, without placing stress on the cells.

DETAILED DESCRIPTION OF THE INVENTION

A culture system and a culture method according to an embodiment of the present invention will be described with reference to the drawings. Cells that are cultured by the culture system and the culture method of the present invention are not limited to adherent cells and they may be floating cells. In a case of culturing adherent cells, a adherent cell mass can be used to allow dispersion of the adherent cells in a solution, or adherent cells can be attached to magnetic particles or a carrier that adsorbs to the magnetic particles (fiber assembly or a porous solid material) to allow dispersion of the adherent cells in a solution. Accordingly, the adherent cells can move together with the solution, and culture can automatically be controlled using height-difference transfer.

Figure 1:
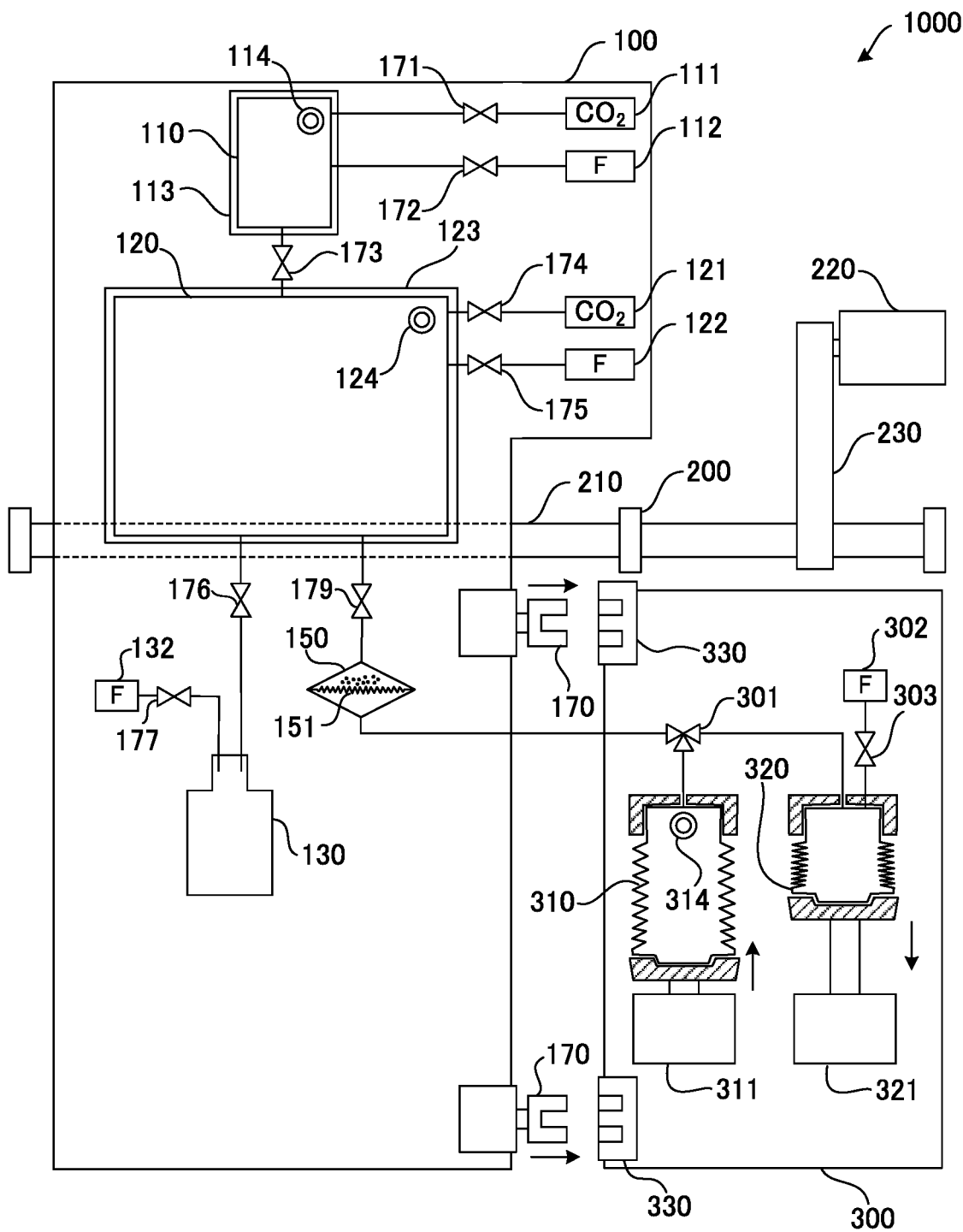
FIG. 1 is a plan view showing a culture system according to an embodiment of the present invention.

A culture system 1000 according to the embodiment of the present invention will be described with reference to FIG. 1. The culture system 1000 is provided with a main stage 100 (first holding section) that performs cell culture, a height-difference imparting mechanism 200 that tilts the stage 100, and a substage 300 (second holding section) that can be connected with the main stage 100. The main stage 100 can be moved between a horizontal state and a vertical state by the height-difference imparting mechanism 200.

The main stage 100 is provided with a preparatory culture vessel 110 having a flat resin culture space, and a main culture vessel 120 having a flat resin culture space. The volume of the preparatory culture vessel 110 is smaller than the volume of the main culture vessel 120. For example, the volume of the preparatory culture vessel 110 may be 10-30 ml or the volume of the main culture vessel 120 may be 100-300 ml. Each of the culture vessels may be disposable. Moreover, although the shape of each culture vessel is a flat cuboid, it is not limited thereto and any shape such as a column or a shape having a bottom surface of a column with a circular cone on it. Furthermore, the inner surface of each culture vessel is preferably treated such that adherent cells do not adhere onto it.

The preparatory culture vessel 110 is provided with a gas supply section 111 for supplying $CO_2$ gas inside the vessel, a ventilation filter 112 for appropriately managing the pressure inside the vessel, a temperature regulating unit 113 for regulating the temperature of the solution inside the vessel, and a feed port 114 for introducing a solution, cells or the like into the vessel. The gas supply section 111 and the ventilation filter 112 are connected to the preparatory culture vessel 110 via a flexible resin connecting tube (conduit). In addition, the preparatory culture vessel 110 and the main culture vessel 120 are also connected with a flexible resin connecting tube. The connecting tubes are provided with valves 171 or 172, respectively. The valve 173 provided on the tube between the preparatory culture vessel 110 and the main culture vessel 120 may be a check valve. The feed port 114 is closed with a cap.

The main culture vessel 120 is provided with a gas supply section 121 for supplying $CO_2$ gas inside the vessel, a ventilation filter 122 for appropriately managing the pressure inside the vessel, a temperature regulating unit 123 for regulating the temperature of the solution inside the vessel to a suitable temperature, and a feed port 124 for introducing a solution, cells or the like into the vessel. The gas supply section 121 and the main culture vessel 120 are connected via a flexible resin connecting tube having a valve 174. The ventilation filter 122 and the main culture vessel 120 are connected via a flexible resin connecting tube equipped with a valve 175. The feed port 124 is closed with a cap.

The gas supply sections 111 and 121 supply gas having a carbon dioxide concentration and a humidity that are required for cell culture from a $CO_2$ gas tank (not shown) into the culture vessel. Preferably, gas conditions with a carbon dioxide concentration of 5%, a humidity of 95%, and a temperature of 37° C. can be employed for the cell culture. The temperature regulating units 113 and 123 are preferably, but not limited to, a temperature managing device such as a thermal cycler, a film heater (sheet heating element) or a coolable and heatable Peltier element. The temperature regulating units 113 and 123 may be provided on both top and bottom surfaces or on the top surface of the preparatory culture vessel 110 or the main culture vessel 120, respectively.

The main culture vessel 120 is connected to a sorting vessel 130 for sorting the cells cultured in the main culture vessel 120 and to a cell capturing unit 150. The sorting vessel 130 is a bottle-shaped vessel. The sorting vessel 130 is connected to a ventilation filter 132 for suitably managing the pressure inside the vessel. A connecting tube between the sorting vessel 130 and the ventilation filter 132 is provided with a valve 177. The cell capturing unit 150 is provided with a filter block 151, which captures the cells in the solution sent from the main culture vessel 120. The solution removed of the cells is sent to the substage 300.

In the main stage 100, a plurality of recesses are formed, which accommodate and hold the preparatory culture vessel 110, the main culture vessel 120, the sorting vessel 130, the cell capturing unit 150, the connecting tubes and the valves 171-179, respectively. As the valves 171-179, solenoid valves that can automatically be opened or closed with a controller or pinchcocks that can manually or automatically be opened or closed can be used.

The height-difference imparting mechanism 200 is provided with a rotation shaft 210 that is integrated with and thus rotates with the main stage 100, a motor 220 and a transmitting mechanism 230 for transmitting the rotation of the motor to the rotation shaft. The transmitting mechanism may be a belt, a gear or the like.

The substage 300 is provided with a feed fluid bellows vessel 310 and a waste fluid bellows vessel 320. The feed fluid bellows vessel 310 is provided with a feed port 314 for introducing a solution into the vessel 310. The feed fluid bellows vessel 310 and the waste fluid bellows vessel 320 are connected to stretching mechanisms 311 and 321 for stretching the respective bellows vessels, respectively. The feed fluid bellows vessel 310 and the waste fluid bellows vessel 320 may be made from a flexible resin and may be disposable. The feed fluid bellows vessel 310 and the waste fluid bellows vessel 320 are connected to the cell capturing unit 150 via a connecting tube equipped with a three-way selector valve (switching mechanism) 301. The three-way selector valve 301 switches between the connection between the cell capturing unit 150 and the feed fluid bellows vessel 310 and the connection between the cell capturing unit 150 and the waste fluid bellows vessel 320. The connection state of the three-way selector valve 301 can be switched by the controller. The feed port 314 is closed with a cap.

The substage 300 also has a plurality of recesses formed, which accommodate and hold the feed fluid bellows vessel 310, the stretching mechanism 311, the waste fluid bellows vessel 320, the stretching mechanism 321, the connecting tubes and the three-way selector valve 301, respectively.

The main stage 100 is provided with a plurality of arm parts 170 that stretch by the controller while the substage 300 is provided with a plurality of arm joints 330 for receiving the plurality of arm parts 170. Once the arm parts 170 elongate and join the arm joints 330, the subunit 300 integrates with the main unit 100 so that the subunit 300 can be rotated together with the main unit.

Hereinafter, an operation of the cell culture system 1000 of the present embodiment will be described.

(Preparatory Culture)

First, the preparatory culture step carried out in the preparatory culture vessel 110 will be described. The main stage 100 and the substage 300 are separately arranged at substantially horizontal culture positions. At these culture positions, cells and a solution are injected from the feed port 114 into the preparatory culture vessel 110 using a dispensing mechanism while $CO_2$ gas at a suitable concentration is supplied from the gas supply section 111. In a state where the cells, the culture solution and the $CO_2$ gas are supplied into the preparatory culture vessel 110, the temperature regulating unit 113 controls the temperature inside the preparatory culture vessel 110 to have a suitable temperature while the motor 220 rotates the rotation shaft 200 at a predetermined angle range to periodically tilt (shake, swing) the main stage 100 as a whole. Due to this tilting, the cells, the culture solution and $CO_2$ in the preparatory culture vessel 110 on the main stage 100 are agitated and undergo culture.

After a predetermined period of time following the initiation of culture where the cells in the preparatory culture vessel 110 have sufficiently been proliferated, the height-difference imparting mechanism 200 rotates the main stage 100 and halts the preparatory culture vessel 110 at a height-difference transfer position. The height-difference transfer position is preferably such that the main stage 100 is kept vertical, but it is not limited thereto as long as there is a tilt that allows the liquid in the preparatory culture vessel 110 to drop by gravity via the connecting tube.

When the valves 172, 173 and 175 are opened at the height-difference transfer position, the solution containing the cells in the preparatory culture vessel 110 is automatically transferred into the main culture vessel 120 by gravity. The valve 172 may be closed and the valve 171 may be opened so that gas is injected from the gas supply section 111 into the preparatory culture vessel 110, which promotes transfer of the solution. At the height-difference transfer position, the valves 176 and 179 are closed.

(Main Culture)

Next, the main culture step carried out in the main culture vessel 120 will be described. Once the solution is completely transferred from the preparatory culture vessel 110 into the main culture vessel 120, the valve 173 is closed, and the main stage 100 is moved to the horizontal culture position. At this culture position, the culture solution is injected from the feed port 124 into the main culture vessel 120 using the dispensing mechanism while $CO_2$ gas at a suitable concentration is supplied from the gas supply section 121. In a state where the cells, the culture solution and the $CO_2$ gas are supplied into the main culture vessel 120, the temperature regulating unit 123 controls the temperature inside the main culture vessel 120 to have a suitable temperature while the motor 220 rotates the rotation shaft 200 at a predetermined angle range to periodically tilt the main stage 100 as a whole. Due to this tilting, the cells, the culture solution and $CO_2$ in the preparatory culture vessel 120 on the main stage 100 are agitated and undergo culture.

(Exchanging Culture Solution)

Continuously, a step of exchanging the culture solution in a case where the culture solution in the main culture vessel 120 is required after a predetermined period of time following initiation of the culture will be described. First, at the culture positions, the arm parts 170 and the arm joints 330 are joined to integrate the main stage 100 and the substage 300. The height-difference imparting mechanism 200 rotates the main stage 100 and the substage 300 such that the main culture vessel 120 is moved upward with respect to the substage 300 and halted at the height-difference transfer position.

At the height-difference transfer position, the valve 176 is kept close while the valves 175 and 179 are opened so as to connect the cell capturing unit 150 and the waste fluid bellows vessel 320 with the three-way selector valve 310 on the substage 300. The solution containing the cells in the main culture vessel 123 is transferred into the cell capturing unit 150 by gravity. In the cell capturing unit 150, the cells are captured on the top surface of the filter block 151 (surface on the valve 179 side), and the solution removed of the cells drops by gravity and is transferred into the contracted waste fluid bellows vessel 320 to be discarded. Since the waste fluid bellows vessel 320 is contracted in advance as shown in FIG. 1, the transfer of the solution from the main culture vessel 123 via the cell capturing unit 150 can be promoted as the waste fluid bellows vessel 320 is elongated using the stretching mechanism 321.

Once the solution is completely discarded, the three-way selector valve 301 separates the waste fluid bellows vessel 320 and the cell capturing unit 150 while the height-difference imparting mechanism 200 moves the main stage 100 and the substage 300 to the fluid feeding positions. At the fluid feeding position, the main stage 100 and the substage 300 are generally vertical while the feed fluid bellows vessel 310 is positioned above the main culture vessel 120. The main stage 100 and the substage 300 are not necessarily vertical as long as the main culture vessel 120 side of the main stage 100 is tilted downward while the feed fluid bellows vessel 310 of the main state 100 and the substage 300 is tilted upward. As the main stage 100 and the substage 300 move from the height-difference transfer positions to the fluid feeding positions, the filter block 151 of the cell capturing unit 150 turns upside down. By this, the cells captured on the top surface of the filter block 151 at the height-difference transfer position will stay on the bottom surface of the filter block 151 at the fluid feeding position.

At the fluid feeding position, the three-way selector valve 301 connects the feed fluid bellows vessel 310 and the cell capturing unit 150 while the valves 179 and 175 are opened. In this state, a new culture solution is transferred by gravity from the feed fluid bellows vessel 310 that has already been injected with the new culture solution beforehand into the cell capturing unit 150. The culture solution is transferred into the main culture vessel 120 together with the cells captured on the bottom surface (valve 179 side) of the filter block 151 of the cell capturing unit 150, thereby completing fluid feeding. Accordingly, the height-difference imparting mechanism 200 is used to turn the cell capturing unit 150 upside down so that the cells can be separated from the culture solution and the cells can be dispersed into the culture solution with the cell capturing unit 150 in an automatic manner. Here, by compressing the feed fluid bellows vessel 310 with the stretching mechanism 311, transfer of the new culture solution can be promoted.

Once the fluid feeding is completed, the height-difference imparting mechanism 200 moves the main stage 100 and the substage 300 to the culture positions to repeat cell culture.

(Cell Sorting)

Finally, the cell sorting step will be described. After a predetermined period of time following the initiation of culture and the cells in the main culture vessel 120 have sufficiently been proliferated, the height-difference imparting mechanism 200 rotates the main stage 100 and halts the main culture vessel 120 at the height-difference transfer position. At the height-difference transfer position, the valves 175, 176 and 177 are opened while the valve 179 is closed and thus the solution containing the cells drops by gravity from the main culture vessel 120 into the sorting vessel 130, where the cells are sorted. Furthermore, by closing the valve 175 and opening the valve 174 to inject gas from the gas supply section 121 into the main culture vessel 120, the transfer of the solution from the main culture vessel 120 into the sorting vessel 130 can be promoted.

(Variation)

Figure 2:
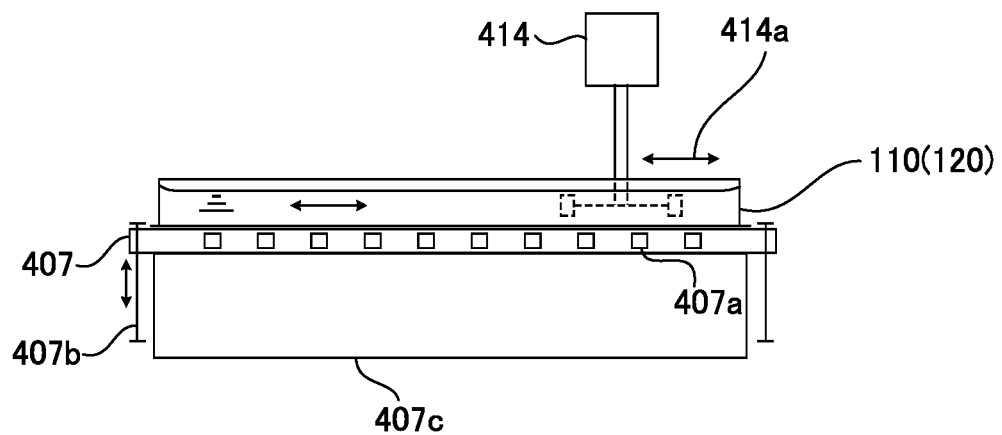
FIG. 2 is a side view showing a variation that can be applied to the culture system shown in FIG. 1.

A variation of the present embodiment will be described with reference to FIGS. 2 and 3. This variation is provided with a sliding mechanism 414 for sliding the preparatory culture vessel 110 and/or the main culture vessel 120, and a magnetic force regulating unit (shaking mechanism) 407 for shaking the solution in the preparatory culture vessel 110 and/or the main culture vessel 120 by magnetic force.

The culture vessel 110 (120) is connected to the sliding mechanism 414 which periodically slides (vibrates) the culture vessel in the horizontal direction as indicated by the arrow 414*a* shown in the figure. The sliding mechanism 414 can be realized by converting the rotation of the motor into linear motion with a rack or a cam. Since the position of the culture vessel 110 (120) alters by the sliding mechanism 414, the connecting tube connected to the culture vessel 110 (120) is arranged to have enough length to maintain the connection even when the position of the culture vessel 110 (120) changes.

The magnetic force regulating unit 407 can get closer to or away from the culture vessel 110 (120) along a guide 407*b* with a magnetic force regulating unit moving mechanism 407*c*. When the magnetic force regulating unit 407 gets closer to the bottom surface of the culture vessel 110 (120), the magnetic force of the magnets 407*a* can concentrate and fix (adsorb) the magnetic particles and the cells contained in the culture solution in the culture vessel 110 (120) on the inner bottom surface of the culture vessel 110 (120). When the magnetic force regulating unit 407 gets away from the bottom surface of the culture vessel 110 (120), the magnetic force of the magnets 407*a* no longer has the effect inside the culture vessel 110 (120), and thus the magnetic particles and the cells move away from the inner bottom surface of the culture vessel 110 (120) and disperse.

Figure 3:
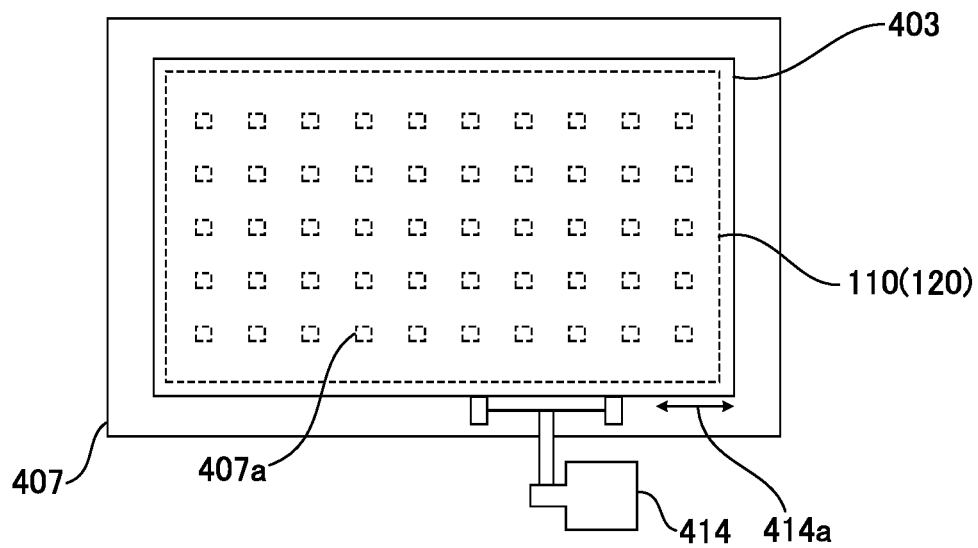
FIG. 3 is a plan view showing the variation of FIG. 2.

As shown in FIG. 3, a plurality of permanent magnets 407*a* are arranged in a matrix, i.e., vertically and horizontally arrayed at regular intervals, in the magnetic force regulating unit 407. Each of the permanent magnets 407*a* included in this array can concentrate and fix the magnetic particles and the cells contained in the culture solution in the culture vessel 110 (120) onto the inner surface of the culture vessel 110 (120). The polarities of the adjacent magnets 407*a* are always opposite. Accordingly, polarities of magnetic particles that adsorbed onto adjacent magnets 407*a* differ from each other and result repulsive force between them, as a result of which the populations of the magnetic particles and the cells adsorbed onto the magnets 407*a* are more likely to concentrate. Here, by providing a magnet for adsorbing magnetic particles on the sorting vessel 130, the magnetic particles can be separated from the cells.

Since conventional culture systems use a cylinder or a pump, they require washing of the cylinder and are also associated with a risk of contamination. The culture vessel, the sorting vessel and the bellows vessel of the culture system of the present embodiment can all essentially be made from plastic and thus can be completely disposable, which can significantly reduce the risk of contamination. Although a risk of contamination increases, a cylinder can be used instead of each bellows vessel. While the solution movement between the respective culture vessels or between the culture vessel and the bellows vessel was realized through dropping using height difference, the solution movement can be promoted by suction with a vacuum pump. Although two culture vessels are used in the present embodiment, the number of the culture vessels is not limited thereto and may be one or three. The controller of the present embodiment is connected to an operating panel, where various settings of the program can be changed to perform culture.

The invention claimed is:
1. A culture system comprising:
a plurality of housing vessels accommodating cells and a solution;
conduits connecting the plurality of housing vessels;
a valve opening and closing the conduits;
a first holding section for holding the plurality of housing vessels;
an agitator imparting a height difference between the plurality of housing vessels in order to allow dropping of the cells and the solution between the plurality of housing vessels,
magnetic particles that are attached to the cells in the solution,
a plurality of magnets provided outside at least one of the plurality of housing vessels, and
a magnetic force regulating unit regulating magnetic forces of the plurality of magnets
wherein the agitator periodically tilts at least one of the plurality of housing vessels to agitate the cells, and the culture solution in the housing vessels when undergoing culture, and
wherein the magnetic force regulating unit has a flat portion on which the plurality of magnets are arranged in a matrix, at least one of the housing vessels has a flat portion, and the flat portion of the magnetic force regulating unit faces the flat portion of at least one of the housing vessels: and
wherein the agitator has a rotation shaft for rotating the first holding section, the plurality of housing vessels are arranged on the first holding section along a direction intersecting with an axial direction of the rotation shaft.

2. The culture system according to claim 1, wherein the agitator imparts a height difference to at least one of the plurality of housing vessels by moving the first holding section.

3. The culture system according to claim 1, wherein the plurality of housing vessels comprises one or a plurality of culture vessels.

4. The culture system according to claim 1, wherein at least one of the plurality of housing vessels is connected to at least one cylinder or bellows vessel.

5. The culture system according to claim 4, wherein the agitator imparts a height difference between at least one of the plurality of the housing vessels and the cylinder or the bellows vessel so as to transfer the cells and the solution between at least one of the plurality of housing vessels and the cylinder or the bellows vessel by dropping.

6. The culture system according to claim 5, wherein the cylinder or the bellows vessel is a waste fluid vessel, and wherein one of the conduits connects between the waste fluid vessel and the at least one of the plurality of the housing vessels, and wherein the one of the conduits is provided with a cell capturing unit.

7. The culture system according to claim 6, wherein the cylinder or the bellows vessel is a feed fluid vessel, which is connected to the cell capturing unit.

8. The culture system according to claim 7, comprising a switching mechanism switching between the connection between the cell capturing unit and the cylinder or the bellows vessel.

9. The culture system according to claim 4, comprising an actuator stretching the cylinder or the bellows vessel.

10. The culture system according to claim 4, comprising a second holding section for holding the cylinder or the bellows vessel.

11. The culture system according to claim 10, wherein the first holding section and the second holding section are detachable.

12. The culture system according to claim 4, wherein the bellows vessel is disposable.

13. The culture system according to claim 1, wherein the housing vessels are provided with a temperature regulating unit.

14. The culture system according to claim 1, wherein the housing vessels are provided with a carbon dioxide supply section.

15. The culture system according to claim 1, wherein the housing vessels are provided with a ventilation section.

16. The culture system according to claim 1, wherein the housing vessels are disposable.

17. The culture system according to claim 1, wherein the agitator also swings the housing vessels.

18. The culture system according to claim 1, further comprising:
wherein the plurality of housing vessels include a culture vessel,
wherein one of the plurality of magnets is provided outside the culture vessel, and
wherein the magnetic force regulating unit regulates a magnetic force of the one of the plurality of magnets provided outside the culture vessel to shake or vibrate the magnetic particles and the cells in the culture vessel.

19. The culture system according to claim 1, further comprising a controller controlling the valve and the agitator,
wherein the controller controls the valve and the agitator according to a predetermined procedure to perform cell culture and transfer the solution in an automatic manner.

20. A method for performing cell culture, comprising:
accommodating cells and a solution by a plurality of housing vessels;
connecting the plurality of housing vessels by conduits;
opening and closing the conduits by a valve;
holding the plurality of housing vessels by a first holding section;
imparting, by an agitator, a height difference between the plurality of housing vessels in order to allow dropping of the cells and the solution between the plurality of housing vessels;
attaching magnetic particles to the cells in the solution;
providing a plurality of magnets outside at least one of the housing vessels;
regulating, by a magnetic force regulating unit, magnetic forces of the plurality of magnets;
periodically tilting, by the agitator, at least one of the plurality of housing vessels to agitate the cells; and the culture solution in the housing vessels when undergoing culture,
wherein the magnetic force regulating unit has a flat portion on which the plurality of magnets are arranged in a matrix, at least one of the housing vessels has a flat portion, and the flat portion of the magnetic force regulating unit faces the flat portion of at least one of the housing vessels,
wherein the agitator has a rotation shaft for rotating the first holding section, the plurality of housing vessels are arranged on the first holding section along a direction intersecting with an axial direction of the rotation shaft.

21. The method according to claim 20, comprising the steps of:
 culturing at a position where the height difference between the plurality of housing vessels is made smaller by the agitator;
 transferring the cells and the solution at a dropping position where the height difference between the plurality of housing vessels is made larger by the agitator; and
 treating the solution using at least one cylinder or bellows vessel connected to at least one of the plurality of housing vessels.

22. The method according to claim 21, wherein the step of treating the solution is a step of discarding the solution or a step of supplying the solution.

* * * * *